ary Examiner—Joseph E. Evans
United States Patent [19]
Buckl et al.

[11] 3,980,719
[45] Sept. 14, 1976

[54] PROCESS FOR OBTAINING XYLITOL FROM NATURAL PRODUCTS CONTAINING XYLAN

[75] Inventors: Hans Buckl, Freising; Rudolf Fahn, Moosburg; Carl Ernst Hofstadt, Munich, all of Germany

[73] Assignee: Sud-Chemie AG, Munich, Germany

[22] Filed: Jan. 4, 1974

[21] Appl. No.: 430,840

Related U.S. Application Data

[63] Continuation of Ser. No. 112,481, Feb. 3, 1971, abandoned.

[30] Foreign Application Priority Data

Feb. 9, 1970 Germany............................ 2005851

[52] U.S. Cl. .......................... 260/635 C; 260/637 R
[51] Int. Cl.² ................... C07C 29/00; C07C 29/24
[58] Field of Search.......... 260/635 C, 643 F, 637 R

[56] References Cited
UNITED STATES PATENTS

| | | | |
|---|---|---|---|
| 2,629,686 | 2/1953 | Grosser | 260/643 F |
| 2,917,390 | 12/1959 | Apel et al. | 260/635 C |
| 2,989,569 | 6/1961 | Apel | 260/635 C |
| 3,367,947 | 2/1968 | Pierson | 260/637 R |
| 3,579,380 | 5/1971 | Friese | 260/635 C |
| 3,586,537 | 6/1971 | Steiner et al. | 260/635 C |

FOREIGN PATENTS OR APPLICATIONS

| | | | |
|---|---|---|---|
| 850,133 | 9/1960 | United Kingdom | 260/635 C |
| 842,743 | 7/1960 | United Kingdom | 260/635 C |

*Primary Examiner*—Joseph E. Evans
*Attorney, Agent, or Firm*—Burgess, Dinklage & Sprung

[57] ABSTRACT

Xylitol which is useful as a sugar substitute is produced from xylan containing natural products by: acid hydrolyzing xylan to xylose; concentrating the hydrolysis solution to remove acetic acid by-product; diluting with water; adjusting the pH to about 6.5 to about 7.5; catalytically hydrogenating the xylose to xylitol under pressure; and recovering xylitol by extraction.

7 Claims, No Drawings

PROCESS FOR OBTAINING XYLITOL FROM NATURAL PRODUCTS CONTAINING XYLAN

This is a continuation of application Ser. No. 112,481, filed Feb. 3, 1971, now abandoned.

BACKGROUND

This invention relates to a process for preparing sugar substitute xylitol from xylan containing natural products by acid hydrolysis and catalytic hydrogenation.

Xylitol is increasingly being used as a sugar substitute for diabetics and as a component of intravenous feeding solutions. Known processes for obtaining xylitol begin by producing xylose by acid decomposition from natural products containing xylan. The xylose contained in the acid decomposition solution is then freed of accompanying substances and isolated in pure form. The pure xylose is then hydrogenated under pressure to form xylitol, whereupon the xylitol is isolated from the hydrogenating solution and obtained in pure form.

These known processes, however have the disadvantage that two separate isolating processes are required, namely the intermediate isolation of xylose and final isolation of xylitol. It has hitherto been thought that hydrogenation of xylose is possible only when the xylose is in the isolated state because the accompanying substances produced in the acid decomposition have a harmful effect on the hydrogenation catalyst. Sometimes the acid decomposition produces acetic acid which reacts with the catalyst and soon renders it useless. This is especially critical in the case of Raney nickel catalysts, and even in the case of noble metal catalysts, such as ruthenium catalysts. The acetic acid in some cases can react with the support which also renders the catalyst useless. Nor does it suffice to neutralize the hydrolysis solution, because the hydrolysis of the acetate that forms is constantly establishing a pH of 5 at which the catalyst or support begins to dissolve.

The isolation of xylose brings about a separation of the glucose that also develops in the decomposition, so that the hydrogenation can produce xylitol only, rather than a xylitol-sorbitol mixture, for it is known that it is less difficult to isolate pure xylitol from an aqueous mixture of xylitol and sorbitol.

SUMMARY

The object of the invention is to devise a process in which isolation of the xylose prior to hydrogenation is not necessary.

The invention thus concerns a process for obtaining xylitol from natural products containing xylan, by acid decomposition and hydrogenation of the xylose that is produced as a decomposition product; the process is characterized by the fact that, the acid xylose solution produced in the decomposition is concentrated by evaporation to a syrupy consistency which removes the acetic acid that is produced as a byproduct, the concentrated syrup is diluted with water and neutralized to a pH of approximately 6.5 to 7.9, the xylose that is still in solution is catalytically hydrogenated to xylitol without prior isolation, and the hydrogenation solution containing the xylitol is subjected to extraction to receover xylitol.

DESCRIPTION

In general the process of this invention is performed as follows:

Woods and natural products containing xylan, such as beechwood, coconut shells, almond shells, straw, oat hulls, etc., are treated with dilute mineral acids, preferably sulfuric acid, at elevated temperatures and under pressure. The decomposition can be performed with 0.1 to 6% acid at about 100° to 180°C and 0 to 10 atmospheres gauge pressure, over a period of ½ hour to 4 hours. The resulting decomposition solution contains about 5 to 15% xylose and about 1 to 4% glucose, plus proteins, tannins, pectins, partially hydrolyzed polysaccharides etc. The solution is cooled to a temperature below 100°C, preferably to about 50° to 80°C, and unhydrolyzed organic residues are removed by filtration. The sulfuric acid is bound as calcium sulfate by the addition of calcium carbonate, a pH of approximately 1.5 to 3.5 being thereby established.

After the separation of the precipitated calcium sulfate, the solution is preferably purified through active charcoal, thereby removing most of the proteins, tannins and pectins. The active charcoal, of a grain size corresponding to an economical rate of flow, is placed, for example, in a vertical column, and the solution to be purified is best fed downward through the column. The treatment with active charcoal, however, can also be performed in other ways, e.g., by stirring the active charcoal into the solution, then filtering it out again.

Substances other than active charcoal can also be used for the purification of the solution, examples being silica gel, aluminum oxide, molocular sieves, etc.

The purified solution still contains about 1 to 2% acetic acid from the hydrolysis, which has to be removed so as to prevent the impairment of the hydrogenation catalyst. This is done by concentrating the purified and neutralized hydrolysis solution (pH 1.5 to 3.5) under a vacuum at a temperature of about 50° to 70°C. The concentration is to be performed until a viscous syrup is obtained which is virtually free of water. Neutralization of the acetic acid or its removal by means of ion exchangers is not desirable, because much of the xylose would be destroyed by very basic ion exchangers which are necessary for the quantitative removal of the acetic acid (probably due to condensation or racemization), and this would greatly diminish the xylitol yield. It is also important that the concentrating temperature not exceed 70°C, since at higher temperatures a considerable part of the xylose would be transformed to furfurol, and this would also diminish the xylitol yield.

The concentrated xylose syrup freed of acetic acid is then diluted with water to a 40 to 70% solution, and this solution is neutralized to a pH of about 6.5 to 7.5, preferably with oxides or carbonates of calcium and/or magnesium.

Through the above-described preliminary treatments it is possible to hydrogenate the xylose contained in the solution directly to xylitol, without first isolating it. Furthermore, the partially hydrolyzed polysacharides which interfere with the hydrogenation of the sugars are removed by the above-described purification by active charcoal or by other adsorbing agents, without requiring another hydrolysis.

Nickel catalysts are preferred as hydrogenation catalysts, preferably in the form of Raney nickel catalysts. Also suitable are nobel metal catalysts such as ruthenium, palladium or platinum catalysts, which are used in the form of supported catalysts, as are other catalysts used in the prior art for sugar hydrogenation.

The hydrogenation can be performed discontinuously or continuously at about 15 to 150 atmospheres gauge pressure, preferably at about 30 to 100 atmospheres, and at temperatures of about 70° to 150°C, preferably about 100°C. The hydrogenation takes between about 1 and 8 hours, depending on the catalyst and the hydrogenation conditions.

After the hydrogenation the catalyst is removed from the solution, and the solution is again treated with active charcoal or other adsorbing agent in order to purify it. It may be necessary to dilute the solution if the hydrogenation has been performed with a more highly concentrated solution. In general, the solid content of the solution amounts to from 10 to 50%.

For removal of the residual ions, the solution is then preferably passed through cation or anion exchangers.

The purified solution, which contains 15 to 25% sorbitol in addition to xylitol, is then concentrated in a vacuum evaporator down to a water content of about 5 to 15%, the temperature not to exceed 85°C. Preferably the concentration is performed at a temperature of about 80°C.

A syrup is thus produced, which is made to crystallize by stirring ethanol into it. It is preferable to add to the ethanol enough water to make the ratio between the ethanol and the total water (the water in the ethanol and in the syrup) amount to approximately 4 to 5 : 1. It has been found that this ratio is particularly favorable for the separation of the xylitol from the sorbitol that occurs as a by-product, because at this ratio virtually all of the xylitol crystallizes out, while the sorbitol remains in solution.

The crystalline xylitol is now separated in a centrifuge from the ethanol and from the sorbitol remaining in solution, and from the non-crystallizable, dissolved components still adhering to it, and it is washed by covering it with 96% ethanol in which the xylitol is virtually insoluble, and then it is dried.

By the method of the invention, 80 to 85% crystalline xylitol can be obtained, having a melting point of 93°to 96°C, with reference to the total sugar content in the hydrolysis solution.

The invention is illustrated further by the following examples.

EXAMPLE 1

60 liters of 0.6% sulfuric acid is added to 12 kg of beechwood chips which are then hydrolyzed for one hour at 135° to 140°C and 3 to 4 atmospheres gauge pressure. The filtered hydrolyzate is purified through active charcoal, and adjusted with calcium carbonate to pH 2 to 2.8; the calcium sulfate that has formed is removed by filtration, and the hydrolyzate is concentrated by evaporation at about 65°C to a viscous, virtually water-free syrup so as to remove the acetic acid that is present. The solution diluted to about 50% is adjusted to pH 5 with about 0.09 kg of CaCo$_3$ and then neutralized with 8–9 g of MgO to a pH of 7 to 7.2. The dilute, neutral solution is then hydrogenated for 6 hours at 110°C and 50 atmospheres gauge pressure with the addition of 2 to 5%, preferably 3%, of Raney nickel. The catalyst is filtered off or centrifuged out, and then the hydrogenation solution is purified with active charcoal and ion exchangers and concentrated under a vacuum at about 80°C. 2.4 kg of syrup remain having a water content of about 5%. To these 2.4 kg of syrup there is added 1.44 liters of ethanol with a water content of about 12%, whereupon the xylitol crystallizes out and is separated by filtration or centrifugation.
Yield:

| | |
|---|---|
| With reference to the beechwood | 17% xylitol |
| With reference to the total sugar content in the hydrolysis solution (MP 93–96°C) | 83% xylitol |

EXAMPLE 2

22.1 kg of coconut shell flour is hydrolyzed with 66.2 kg of 0.6% sulfuric acid under the conditions described in Example 1. The hydrolysis solution obtained is purified, hydrogenated and further processed in the manner specified in Example 1. The crystallization of the syrup (water content about 5%) is performed by the addition of 60 ml of ethanol (water content about 12%) per kilogram of syrup.
Yield:

| | |
|---|---|
| With reference to the coconut shell flour | 20% xylitol |
| With reference to the total sugar content in the hydrolysis solution (MP 93–96°C) | 85% xylitol |

What is claimed is:
1. Process for preparing xylitol which consists essentially of:
   a. acid hydrolyzing a xylan containing material to produce a solution containing xylose and acetic acid;
   b. recovering unhydrolyzed organic residues by filtration.
   c. removing hydrolyzing acid;
   d. removing most, if any, proteins, tannins and pectins from said solution by contacting the same with an adsorbent;
   e. evaporating said purified solution under vacuum to a viscous, virtually water-free syrup, thereby removing substantially all of the acetic acid in said solution;
   f. diluting said syrup with water and adjusting the pH of the resulting diluted solution to a value of from about 6.5 to about 7.5;
   g. hydrogenating xylose in said diluted solution in the presence of a Raney nickel hydrogenation catalyst under pressure to produce a solution containing xylose; and
   h. recovering xylitol from the xylitol containing solution.

2. Process for preparing xylitol which consists essentially of:
   a. acid hydrolyzing a xylan containing material to produce a solution containing xylose and acetic acid;
   b. removing unhydrolyzed organic residues by filtration;
   c. removing hydrolyzing acid;
   d. removing most, if any, proteins, tannins and pectins from said solution by contacting the same with an adsorbent;
   e. evaporating said purified solution at a temperature not in excess of 70°C under vacuum to a viscous, virtually water-free syrup thereby removing substantially all of the acetic acid in said solution;

f. diluting said syrup with water and adjusting the pH of the resultant diluted solution to a value of from about 6.5 to about 7.5;

g. without any acid removal step performed on said syrup or the resultant diluted syrup, hydrogenating the xylose in said diluted solution in the presence of a Raney nickel hydrogenation catalyst under pressure to produce a solution containing xylitol; and h. recovering xylitol from the xylitol containing solution.

3. Process of claim 1, wherein one or more oxides or carbonates of calcium or magnesium are used to adjust the pH of the xylose containing solution.

4. Process of claim 1 wherein the hydrogenation is carried out at about 15 to about 150 atmospheres gauge pressure and about 70° to 150°C.

5. Process of claim 1 wherein a purification with active charcoal is carried out before and after the hydrogenation.

6. Process of claim 1 wherein residual ions are removed by cation or anion exchangers after the hydrogenation.

7. Process of claim 1 wherein the xylitol containing solution is concentrated by evaporation to a syrupy consistency and the syrup diluted with ethanol, the weight ratio between ethanol and total water amounting to approximately 4 to 5 : 1.

\* \* \* \* \*